United States Patent
Takada et al.

(10) Patent No.: US 9,242,992 B2
(45) Date of Patent: Jan. 26, 2016

(54) CRYSTAL FORM OF TRICYCLIC BENZOPYRAN COMPOUND AND PRODUCTION METHOD THEREOF

(75) Inventors: Yasutaka Takada, Funabashi (JP); Miyako Kamon, Funabashi (JP); Shiro Kawahara, Funabashi (JP); Yasuhiro Umeda, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 352 days.

(21) Appl. No.: 13/318,230

(22) PCT Filed: Apr. 30, 2010

(86) PCT No.: PCT/JP2010/057698
§ 371 (c)(1),
(2), (4) Date: Nov. 16, 2011

(87) PCT Pub. No.: WO2010/126138
PCT Pub. Date: Nov. 4, 2010

(65) Prior Publication Data
US 2012/0059169 A1  Mar. 8, 2012

(30) Foreign Application Priority Data
Apr. 30, 2009  (JP) .................................. 2009-111281

(51) Int. Cl.
*C07D 491/052*   (2006.01)
(52) U.S. Cl.
CPC .................. *C07D 491/052* (2013.01)
(58) Field of Classification Search
CPC ................................................ C07D 491/052
USPC ...................... 546/80, 89; 514/291
See application file for complete search history.

(56) References Cited

FOREIGN PATENT DOCUMENTS

WO    WO 2005/090357 A1    9/2005

OTHER PUBLICATIONS

Detection of Polymorphism by Powder X ray diffraction: Interference by preferred orientation, M. Davidovich et al 2004.*
Ashizawa; "Iyakuhin no kesshoutakei to shouseki no kagaku (Science of crystal polymorphism and crystallization of drugs);" 2002; pp. 392-393; Maruzen Plant Co., Ltd. (with Abstract).
Yamano; "Shin'yaku no Process Kenkyu to Kessho Takei Gensho;" *Farumashia (Pharmacia)*; Apr. 1, 2009; pp. 327-332; vol. 45, No. 4 (with Abstract).
International Search report dated Jul. 13, 2010 in International Application No. PCT/JP2010/057698 (with translation).
Written Opinion of the International Searching Authority dated Jul. 13, 2010 in International Application No. PCT/JP2010/057698.
Brittain et al., "Polymorphism in Pharmaceutical Solids", (Chapter 1) p. 1-10, (Chapter 5) p. 183-226, 1999.
Caria, "Crystalline Polymorphism of Organic Compounds", Topics of Current Chemistry, vol. 198, p. 163-208, 1998.
Byrn et al., "Pharmaceutical Solids: A Strategic Approach to Regulatory Considerations", Pharmaceutical Research, vol. 12 No. 7, p. 945-954 (1995).
Chawla et al., "Challenges in Polymorphism of Pharmaceuticals", Review Article, CRIPS, vol. 5, p. 9-12 (2004).

* cited by examiner

*Primary Examiner* — Rita Desai
(74) *Attorney, Agent, or Firm* — Oliff PLC

(57) ABSTRACT

Crystal forms of (3R,4S)-7-hydroxymethyl-2,2,9-trimethyl-4-(phenethylamino)-3,4-dihydro-2H-pyrano[2,3-g]quinolin-3-ol that are excellent as a drug, and production methods thereof. Production methods include crystallizing (3R,4S)-7-hydroxymethyl-2,2,9-trimethyl-4-(phenethylamino)-3,4-dihydro-2H-pyrano[2,3-g]quinolin-3-ol from an acetate ester solvent, an aliphatic hydrocarbon solvent, a nitrile solvent, an aromatic hydrocarbon solvent, a ketone solvent or an ether solvent, and crystal forms obtained according to the methods.

21 Claims, 9 Drawing Sheets

INTENSITY (cps)

Intensity (cps)

CRYSTAL FORM OF TRICYCLIC BENZOPYRAN COMPOUND AND PRODUCTION METHOD THEREOF

TECHNICAL FIELD

The present invention relates to crystal forms of (3R,4S)-7-hydroxymethyl-2,2,9-trimethyl-4-(phenethylamino)-3,4-dihydro-2H-pyrano[2,3-g]quinolin-3-ol and production methods thereof.

BACKGROUND ART (3R,4S)-7-hydroxymethyl-2,2,9-trimethyl-4-(phenethylamino)-3,4-dihydro-2H-pyrano[2,3-g]quinolin-3-ol (hereinafter, called as Compound (1)) of Formula (1):

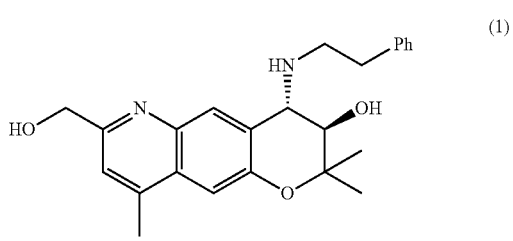

exerts an antiarrhythmic action and the possibility thereof to be used as a drug is known.

Drugs are desired to provide a compound having a constant quality with which a constant effectiveness can be always expected, and are thus generally crystallized. In addition, by crystallizing a compound, there can be obtained such an advantage that the chemical stability of the compound is enhanced (for example, see Non-patent Document 1). Meanwhile, it is known that a solid material has an ability that two or more crystallographic structures different from each other can be taken. The two or more crystallographic structures of the material as described above are called crystal polymorphism. In addition, when a compound is crystallized in an organic solvent or water, it is also known that the organic solvent or water used for the crystallization is sometimes incorporated in the compound, so that the compound becomes a solvate crystal (solvate) or a hydrate crystal (hydrate). In the present specification, the crystal polymorphism together with the solvate crystal and the hydrate crystal are called as crystal forms. These crystal forms usually have different solubilities, dissolution rates, stabilities, hygroscopicities, melting points, handling properties, and the like, so that for developing a crystal of a compound as a drug, it is necessary to evaluate these characteristics comprehensively and to select a crystal form suitable for the development of the drug (for example, see Non-patent Document 2).

However, with respect to Compound (1), there is hitherto only a description that the compound is obtained by the purification using column chromatography and the crystal form of Compound (1) is unknown (for example, see Patent Document 1). It is necessary to confirm whether the compound is able to be crystallized and have crystal forms. Then, when the crystal forms exist, it is necessary to confirm the reproducible production methods of chemically stable crystal forms, and novel crystal forms of the compound.

RELATED-ART DOCUMENTS

Patent Documents

[Patent Document 1] International Publication No. WO 2005/090357 pamphlet

Non-Patent Documents

[Non-patent Document 1]
"Iyakuhin no kesshoutakei to shouseki no kagaku (Science of crystal polymorphism and crystallization of drugs)" edited and written by Kazuhide Ashizawa, p. 392, published by Maruzen Planet Co., Ltd.
[Non-patent Document 2]
"Farumashia" vol. 45, No. 4, p. 327 (2009)

SUMMARY OF THE INVENTION

Problems to be Solved by the Invention

For developing (3R,4S)-7-hydroxymethyl-2,2,9-trimethyl-4-(phenethylamino)-3,4-dihydro-2H-pyrano[2,3-g]quinolin-3-ol as a drug, the possibility of crystallization of the compound and the presence of the crystal forms of the compound are confirmed, and when the crystal forms exist, it is required to confirm reproducible production methods of chemically stable crystal forms, and novel crystal forms of the compound.

Means for Solving the Problems

As a result of assiduous research intended to overcome these problems, the present inventors elucidate that (3R,4S)-7-hydroxymethyl-2,2,9-trimethyl-4-(phenethylamino)-3,4-dihydro-2H-pyrano[2,3-g]quinolin-3-ol can be crystallized and further, at least six types of crystal forms of the compound exist.

Specifically, the present invention is constituted of the followings.

(I)

An A-form crystal of (3R,4S)-7-hydroxymethyl-2,2,9-trimethyl-4-(phenethylamino)-3,4-dihydro-2H-pyrano[2,3-g]quinolin-3-ol of Formula (1):

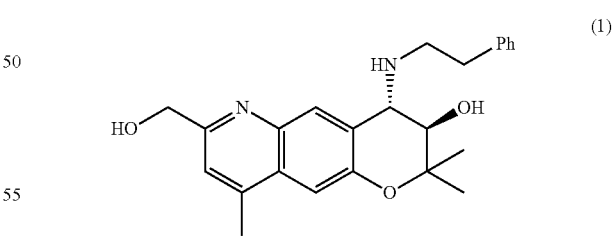

having characteristic peaks at diffraction angles (2θ) of 5.6, 8.2, 12.0, 14.7, 16.6, 16.9, 17.9, 18.4, 22.5, 24.5, 27.6 in a powder X-ray diffractogram of the crystal.

(II)

A production method of an A-form crystal of (3R,4S)-7-hydroxymethyl-2,2,9-trimethyl-4-(phenethylamino)-3,4-dihydro-2H-pyrano[2,3-g]quinolin-3-ol, characterized by comprising crystallizing the compound of Formula (1) in an ester solvent.

(III)

A production method of an A-form crystal of (3R,4S)-7-hydroxymethyl-2,2,9-trimethyl-4-(phenethylamino)-3,4-dihydro-2H-pyrano[2,3-g]quinolin-3-ol, characterized by comprising crystallizing the compound of Formula (1) in an aliphatic hydrocarbon solvent.

(IV)

A production method of an A-form crystal of (3R,4S)-7-hydroxymethyl-2,2,9-trimethyl-4-(phenethylamino)-3,4-dihydro-2H-pyrano[2,3-g]quinolin-3-ol, characterized by comprising crystallizing the compound of Formula (1) in a nitrile solvent.

(V)

A production method of an A-form crystal of (3R,4S)-7-hydroxymethyl-2,2,9-trimethyl-4-(phenethylamino)-3,4-dihydro-2H-pyrano[2,3-g]quinolin-3-ol, characterized by comprising crystallizing the compound of Formula (1) in an aromatic hydrocarbon solvent.

(VI)

A production method of an A-form crystal of (3R,4S)-7-hydroxymethyl-2,2,9-trimethyl-4-(phenethylamino)-3,4-dihydro-2H-pyrano[2,3-g]quinolin-3-ol, characterized by comprising crystallizing the compound of Formula (1) in a ketone solvent.

(VII)

A B-form crystal of (3R,4S)-7-hydroxymethyl-2,2,9-trimethyl-4-(phenethylamino)-3,4-dihydro-2H-pyrano[2,3-g]quinolin-3-ol of Formula (1):

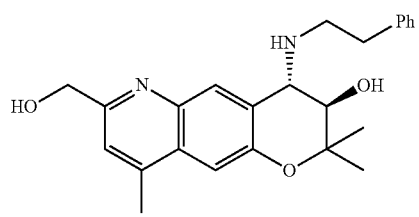

(1)

having characteristic peaks at diffraction angles (2θ) of 6.4, 8.7, 12.8, 17.5, 19.1, 20.7, 22.0, 24.8, 26.6 in a powder X-ray diffractogram of the crystal.

(VIII)

An E-form crystal of (3R,4S)-7-hydroxymethyl-2,2,9-trimethyl-4-(phenethylamino)-3,4-dihydro-2H-pyrano[2,3-g]quinolin-3-ol of Formula (1):

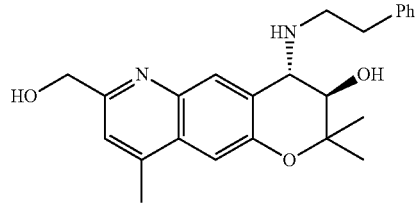

(1)

having characteristic peaks at diffraction angles (2θ) of 9.1, 12.8, 13.1, 14.6, 15.2, 16.4, 22.1, 23.6, 24.8 in a powder X-ray diffractogram of the crystal.

(IX)

An F-form crystal of (3R,4S)-7-hydroxymethyl-2,2,9-trimethyl-4-(phenethylamino)-3,4-dihydro-2H-pyrano[2,3-g]quinolin-3-ol of Formula (1):

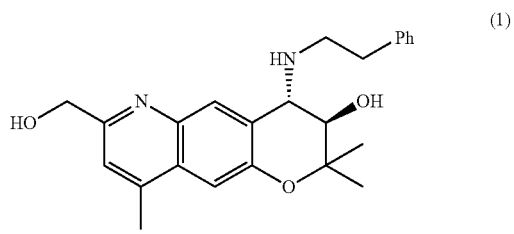 [SMILES: Cc1cc(CO)nc2cc3c(cc12)OC(C)(C)[C@H](O)[C@H]3NCCc1ccccc1]

(1)

having characteristic peaks at diffraction angles (2θ) of 6.8, 11.7, 13.7, 16.8, 18.0, 19.3, 20.4, 20.8, 24.6, 25.6 in a powder X-ray diffractogram of the crystal.

(X)

A G-form crystal of (3R,4S)-7-hydroxymethyl-2,2,9-trimethyl-4-(phenethylamino)-3,4-dihydro-2H-pyrano[2,3-g]quinolin-3-ol of Formula (1):

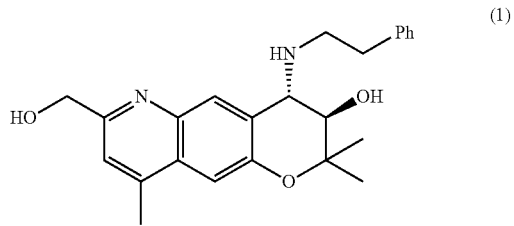 [SMILES: Cc1cc(CO)nc2cc3c(cc12)OC(C)(C)[C@H](O)[C@H]3NCCc1ccccc1]

(1)

having characteristic peaks at diffraction angles (2θ) of 6.7, 11.6, 11.9, 13.6, 16.6, 17.7, 18.6, 19.1, 19.8, 20.1, 20.8 in a powder X-ray diffractogram of the crystal.

(XI)

An H-form crystal of (3R,4S)-7-hydroxymethyl-2,2,9-trimethyl-4-(phenethylamino)-3,4-dihydro-2H-pyrano[2,3-g]quinolin-3-ol of Formula (1):

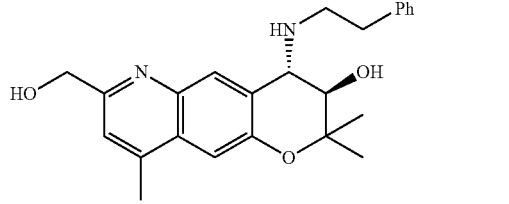

(1)

having characteristic peaks at diffraction angles (2θ) of 6.0, 16.4, 17.0, 19.2, 19.8, 20.3, 21.0, 22.8 in a powder X-ray diffractogram of the crystal.

(XII)

A production method of a B-form crystal of (3R,4S)-7-hydroxymethyl-2,2,9-trimethyl-4-(phenethylamino)-3,4-dihydro-2H-pyrano[2,3-g]quinolin-3-ol, characterized by comprising crystallizing the compound of Formula (1) from a water-containing organic solvent.

(XIII)

A production method of an E-form crystal of (3R,4S)-7-hydroxymethyl-2,2,9-trimethyl-4-(phenethylamino)-3,4-dihydro-2H-pyrano[2,3-g]quinolin-3-ol, characterized by comprising: heating and dissolving the compound of Formula (1) in an acetate ester solvent or a ketone solvent; and performing one shot addition of an aliphatic hydrocarbon solvent and crash cooling.

(XIV)

A production method of an F-form crystal of (3R,4S)-7-hydroxymethyl-2,2,9-trimethyl-4-(phenethylamino)-3,4-dihydro-2H-pyrano[2,3-g]quinolin-3-ol, characterized by comprising crystallizing the compound of Formula (1) from ethanol.

(XV)

A production method of a G-form crystal of (3R,4S)-7-hydroxymethyl-2,2,9-trimethyl-4-(phenethylamino)-3,4-dihydro-2,4-pyrano[2,3-g]quinolin-3-ol, characterized by comprising crystallizing the compound of Formula (1) from 2-propanol.

(XVI)

A production method of an H-form crystal of (3R,4S)-7-hydroxymethyl-2,2,9-trimethyl-4-(phenethylamino)-3,4-dihydro-2H-pyrano[2,3-g]quinolin-3-ol, characterized by comprising: heating and dissolving the compound of Formula (1) in an ether solvent; and performing one shot addition of cyclohexane and crash cooling.

BEST MODES FOR CARRYING OUT THE INVENTION

First, the production method of the A-form crystal is described.

Examples of the ester solvent to be used include: formate esters having a $C_{1-3}$ alkoxy group such as methyl formate, ethyl formate and n-propyl formate; and acetate esters having a $C_{1-4}$ alkoxy group such as methyl acetate, ethyl acetate, n-propyl acetate, isopropyl acetate, n-butyl acetate, isobutyl acetate and tert-butyl acetate, and among them, preferred are ethyl acetate, n-propyl acetate and isopropyl acetate.

Examples of the aliphatic hydrocarbon solvent to be used include $C_{5-7}$ aliphatic hydrocarbons such as pentane, n-hexane, cyclohexane, n-heptane and methylcyclohexane, and among them, n-heptane is preferred.

Examples of the nitrile solvent to be used include $C_{2-4}$ nitriles such as acetonitrile, propionitrile and butylonitrile, and among them, acetonitrile is preferred.

Examples of the aromatic hydrocarbon solvent to be used include $C_{6-8}$ aromatic hydrocarbons such as benzene, toluene and xylene, and among them, preferred are toluene and xylene.

Examples of the ketone solvent to be used include $C_{3-6}$ ketones such as acetone, methyl ethyl ketone, methyl isopropyl ketone and methyl isobutyl ketone, and among them, preferred are acetone and methyl isobutyl ketone.

In addition, only one of these solvents or the mixture of these solvents may be used, and other solvents may be added.

The amount of the solvent to be used is 1 to 50 time(s) by weight, preferably 2 to 20 times by weight, further preferably 5 to 10 times by weight, relative to 1 of the weight of Compound (1).

When the crystallization is performed by cooling a solution of Compound (1), the temperature for the cooling may be a certain temperature between 0° C. and a reflux temperature of the solvent, however preferably, the crystallization is performed by cooling the solution to between 0° C. and 5° C.

When the crystallization is performed by concentrating a solution of Compound (1), the crystallization can be performed by leaving any amount of the solvent or by fully removing the solvent.

In addition, the crystallization can be performed by a combination of both operations of cooling and concentrating.

A seed crystal can be used for crystallization. The seed crystal can be prepared according to a well-known method, for example, by scratching with a spatula the inner wall of the flask containing a solution to be crystallized.

Next, the production method of a B-form crystal which is a hydrate of Compound (1) is described.

The organic solvent to be used is not limited so long as the solvent is miscible with water, and examples of the organic solvent usable include an alcohol solvent, a nitrile solvent, an ether solvent, a ketone solvent, an amide solvent and a sulfoxide solvent. Preferred examples of such solvents include: methanol, ethanol, 1-propanol and 2-propanol as the alcohol solvent; acetonitrile and propionitrile as the nitrile solvent; tetrahydrofuran, 1,2-dimethoxyethane and 1,4-dioxane as the ether solvent; acetone and methyl ethyl ketone as the ketone solvent; N,N-dimethylformamide and N,N-dimethylacetoamide as the amide solvent; and dimethyl sulfoxide as the sulfoxide solvent. Further preferred examples of the organic solvent include methanol, ethanol, 2-propanol, acetonitrile and acetone.

As the water content of the water-containing organic solvent to be used, any water content capable of temporarily dissolving Compound (1) can be selected. Taking a balance between crystallization efficiency and purification effect into account, a mixing ratio of the organic solvent to water preferably ranges from 1:4 to 10:1, more preferably from 1:2 to 3:1.

The crystallization can be performed either by a method including: preparing a water-containing organic solvent beforehand; and heating and dissolving Compound (I) in the prepared organic solvent to cool down the resultant solution, or by a method including: dissolving Compound (1) in an organic solvent; and adding water to the resultant solution. In both methods, the crystallization can be performed by cooling, by concentrating, or by a combination of cooling and concentration.

As the amount of the organic solvent to be used, any amount sufficient to dissolve Compound (1) can be set. However, the amount is preferably 1 to 100 time(s) by weight, more preferably 2 to 50 times by weight, further preferably 5 to 20 times by weight, relative to 1 of the weight of Compound (1).

Next, the production method of the E-form crystal is described.

Examples of the acetate ester solvent to be used include acetate esters having a $C_{1-4}$ alkoxy group such as methyl acetate, ethyl acetate, n-propyl acetate, isopropyl acetate, n-butyl acetate, isobutyl acetate and tert-butyl acetate. Among them, preferred are ethyl acetate, n-propyl acetate and isopropyl acetate and particularly ethyl acetate is preferred.

As the amount of the acetate ester solvent to be used, any amount sufficient to dissolve Compound (1) can be used, however, the amount is preferably 4 to 20 times by volume, particularly preferably 5 to 10 times by volume, relative to 1 of the weight of Compound (1).

Examples of the ketone solvent to be used include $C_{3-6}$ ketones such as acetone, methyl ethyl ketone, methyl isopropyl ketone and methyl isobutyl ketone. Among them, preferred are acetone and methyl isobutyl ketone, and particularly methyl isobutyl ketone is preferred.

As the amount of the ketone solvent to be used, any amount sufficient to dissolve Compound (1) can be used. However, the amount is preferably 5 to 50 times by volume, most preferably 10 to 30 times by volume, relative to 1 of the weight of Compound (1).

Examples of the aliphatic hydrocarbon solvent to be used include $C_{5-7}$ aliphatic hydrocarbons such as pentane, n-hexane, cyclohexane, n-heptane and methylcyclohexane. Among them, preferred are n-hexane and n-heptane and particularly n-heptane is preferred.

The amount of the aliphatic hydrocarbon solvent to be used is preferably 1 to 100 time(s) by volume, more preferably 5 to 50 times by volume, most preferably 10 to 30 times by volume, relative to 1 of the weight of Compound (1).

The crystallization of Compound (1) can be performed at a certain temperature between 0° C. and a reflux temperature of a solvent. However, preferred is a method including: dissolving Compound (1) in an acetate ester solvent or a ketone solvent at 60° C. to 70° C.; and adding an aliphatic hydrocarbon solvent rapidly to the resultant solution and crash cooling the solution to room temperature to be crystallized. Here, "rapidly" means "within 30 seconds".

Then, the production method of an F-form crystal which is an ethanol-solvate of (3R,4S)-7-hydroxymethyl-2,2,9-trimethyl-4-(phenethylamino)-3,4-dihydro-2H-pyrano[2,3-g]quinolin-3-ol is described.

The solvent to be used is ethanol.

The amount of the ethanol to be used is 1 to 50 time(s) by weight, preferably 2 to 20 times by weight, further preferably 3 to 10 times by weight, relative to 1 of the weight of Compound (1).

The crystallization of Compound (1) can be performed at a certain temperature between 0° C. and a reflux temperature of a solvent. However, the crystallization is preferably performed by a method including: heating and dissolving Compound (1) in ethanol in an amount as small as possible; and cooling the resultant solution, by a method including: dissolving Compound (1) in ethanol; and concentrating the resultant solution, or by a method of a combination of the above two methods.

Next, the production method of a G-form crystal which is a 2-propanol-solvate of (3R,4S)-7-hydroxymethyl-2,2,9-trimethyl-4-(phenethylamino)-3,4-dihydro-2H-pyrano[2,3-g]quinolin-3-ol is described.

The solvent to be used is 2-propanol.

The amount of the 2-propanol to be used is 1 to 50 time(s) by weight, preferably 2 to 20 times by weight, further preferably 3 to 10 times by weight, relative to 1 of the weight of Compound (1).

The crystallization of Compound (1) can be performed at a certain temperature between 0° C. and a reflux temperature of a solvent. However, the crystallization is preferably performed by a method including: heating and dissolving Compound (1) in 2-propanol in an amount as small as possible; and cooling the resultant solution, by a method including: dissolving Compound (1) in 2-propanol; and concentrating the resultant solution, or by a method of a combination of the above two methods. Further, the G-form crystal can be obtained only by suspending Compound (1) in 2-propanol.

Next, the production method of an H-form crystal which is a cyclohexane-solvate of (3R,4S)-7-hydroxymethyl-2,2,9-trimethyl-4-(phenethylamino)-3,4-dihydro-2H-pyrano[2,3-g]quinolin-3-ol is described.

The solvent to be used is an ether-based solvent, preferably dioxane.

The amount of dioxane to be used is 1 to 50 time(s) by weight, preferably 2 to 20 times by weight, further preferably 3 to 10 times by weight, relative to 1 of the weight of Compound (1).

The solvent to be used is a cyclohexane.

The amount of cyclohexane to be used is 1 to 50 time(s) by weight, preferably 2 to 20 times by weight, relative to 1 of the weight of Compound (1).

The crystallization of Compound (1) is preferably performed by a method including: dissolving Compound (1) in an ether-based solvent in an amount as small as possible at 60° C. to 70° C.; and adding a cyclohexane rapidly to the resultant solution and crash cooling the solution to room temperature to be crystallized. Here, "rapidly" means "within 30 seconds".

EXAMPLES

Figure 1:
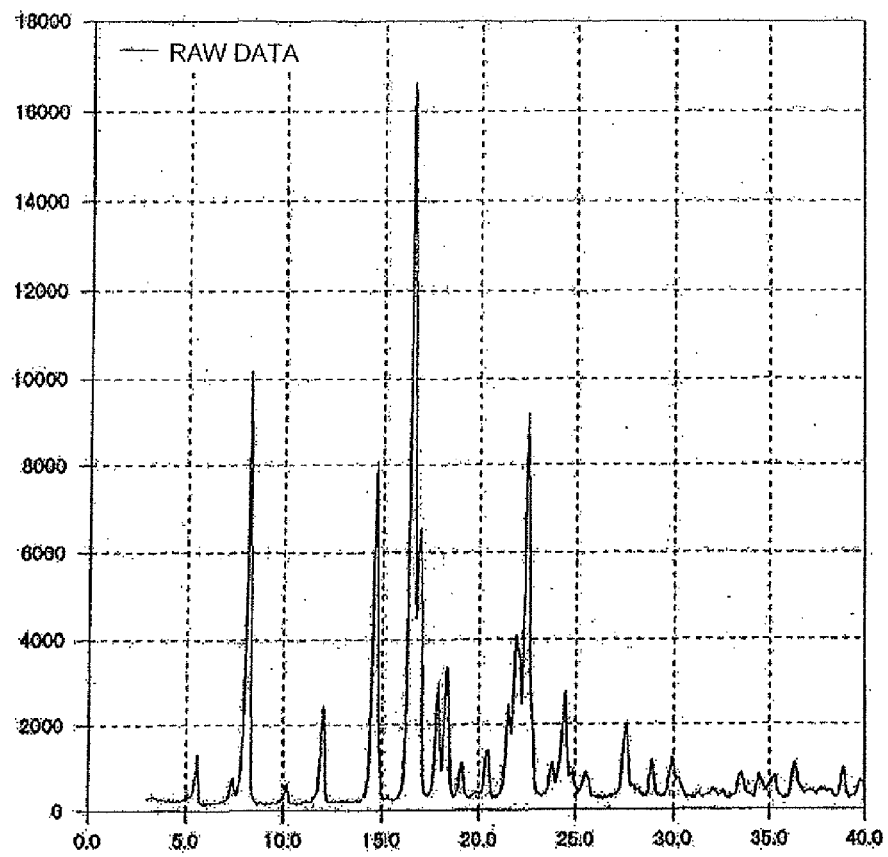
FIG. 1 is a powder X-ray diffractogram of an A-form crystal of (3R,4S)-7-hydroxymethyl-2,2,9-trimethyl-4-(phenethylamino)-3,4-dihydro-2H-pyrano[2,3-g]quinolin-3-ol obtained according to the present invention.

Hereinafter, the present invention will be described in more detail referring to Examples which should not be construed as limiting the scope of the present invention. In Examples the melting point measurement was performed by a capillary method using B-545 (manufactured by Shibata Scientific Technology Ltd.) (temperature rising rate: l°C/min.); the differential scanning calorimetry (DSC) was performed using DSC 8230 (manufactured by Rigaku Corporation) (temperature rising rate: l°C/min.); and the powder X-ray diffraction measurement was performed using MXLabo (manufactured by Mac Science Co., Ltd.; ray source: Cu.Kα, wavelength: 1.54056 ($10^{-10}$ m)).

A crude product of (3R,4S)-7-hydroxymethyl-2,2,9-trimethyl-4-(phenethylamino)-3,4-dihydro-2H-pyrano[2,3-g]quinolin-3-ol (Compound (1)) can be obtained by a method (Synthetic method A) described in International Publication No. WO 2005/090357 pamphlet.

In addition, Compound (1) can be synthesized also by the following method (Synthetic method B).

Reference Synthetic Example 1

Synthesis (Synthetic Method B) of (3R,4S)-7-hydroxymethyl-2,2,9-trimethyl-4-(phenethylamino)-3,4-dihydro-2H-pyrano[2,3-g]quinolin-3-ol 10.05 g (32.1 mmol) of (3R,4S)-(3,4-epoxy-2,2,9-trimethyl-3,4-dihydro-2H-pyrano[2,3-g]quinolin-7-yl)-methyl acetate (synthesized according to a method described in International Publication No. WO 2005/090357 pamphlet) was dissolved in 99.79 g of methanol and into the resultant solution, 40 mL (40 mmol) of a 1M sodium hydroxide aqueous solution was dropped, followed by stirring the resultant mixture at room temperature for 30 minutes. To the resultant reaction mixture, 60.06 g of chloroform and 60.30 g of $H_2O$ were added and the layers were separated, followed by extracting the reaction mixture with chloroform two times. The organic layer was concentrated to produce 9.53 g of a pale brown solid. To the solid, 49.85 g of toluene was added and the resultant suspension was stirred at 60° C. for 10 minutes and cooled down to 5° C. or below to filter the crystal. The crystal was washed with 10.0 g of toluene and dried at 50° C. under reduced pressure to produce 7.98 g (yield: 91.7%) of (3R,4S)-3,4-epoxy-7-hydroxymethyl-2,2,9-trimethyl-3,4-dihydro-2H-pyrano[2,3-g]quinolin-3-ol as a white solid.

Appearance: white solid
$^1$H-NMR (CDCl$_3$, TMS)
δ ppm: 1.31 (3H, s, Me), 1.65 (3H, s, Me), 2.59 (3H, s, Me), 3.60 (1H, d, J=4.3 Hz, C3), 4.15 (1H, d, J=4.3 Hz, C4), 4.42 (1H, t, J=4.0 Hz, CH$_2$OH), 4.83 (2H, d, J=4.0 Hz, CH$_2$OH), 7.07 (1H, s, Ar), 7.31 (1H, s, Ar), 8.08 (1H, s, Ar).

Melting point: 143 to 144° C.

To a liquid mixture of 7.98 g (29.4 mmol) of the obtained (3R,4S)-3,4-epoxy-7-hydroxymethyl-2,2,9-trimethyl-3,4-dihydro-2H-pyrano[2,3-g]quinolin-3-ol and 16.07 g of 1-propanol, 4.30 g (35.5 mmol, 1.2 equivalent) of 2-phenylethylamine was added and the resultant mixture was heated and refluxed for 5 hours. The solvent was distilled off to produce 14.52 g of (3R,4S)-7-hydroxymethyl-2,2,9-trimethyl-4-(phenethylamino)-3,4-dihydro-2H-pyrano[2,3-g]quinolin-3-ol as a brown oily substance.

Example 1

Production of an A-Form Crystal of (3R,4S)-7-hydroxymethyl-2,2,9-trimethyl-4-(phenethylamino)-3,4-dihydro-2H-pyrano[2,3-g]quinolin-3-ol To 14.52 g of a crude product of (3R,4S)-7-hydroxymethyl-2,2,9-trimethyl-4-(phenethylamino)-3,4-dihydro-2H-pyrano[2,3-g]quinolin-3-ol obtained in Reference Synthetic Example 1, 12.02 g of ethyl acetate was added and the resultant mixture was heated to 50° C. to be dissolved, followed by dropping 59.94 g of n-heptane into the resultant solution at 49 to 58° C. to be crystallized. The resultant mixture was cooled down continuously to 3° C. and then the crystal was filtered, followed by washing the crystal with the mixture of 1.5 g of ethyl acetate and 7.5 g of n-heptane and then, with 8.0 g of n-heptane to produce 10.02 g of A-form crystal of Compound (1) as a white crystal. The melting point of the obtained crystal was 124 to 125° C. The obtained crystal was subjected to DSC analysis and as the result, an endothermic peak was confirmed at 130° C. In the powder X-ray diffractogram of the crystal, characteristic peaks were observed at diffraction angles (2θ) of 5.6, 8.2, 12.0, 14.7, 16.6, 16.9, 17.9, 18.4, 22.5, 24.5, 27.6, The result is shown in FIG. 1.

Example 2

Figure 2:
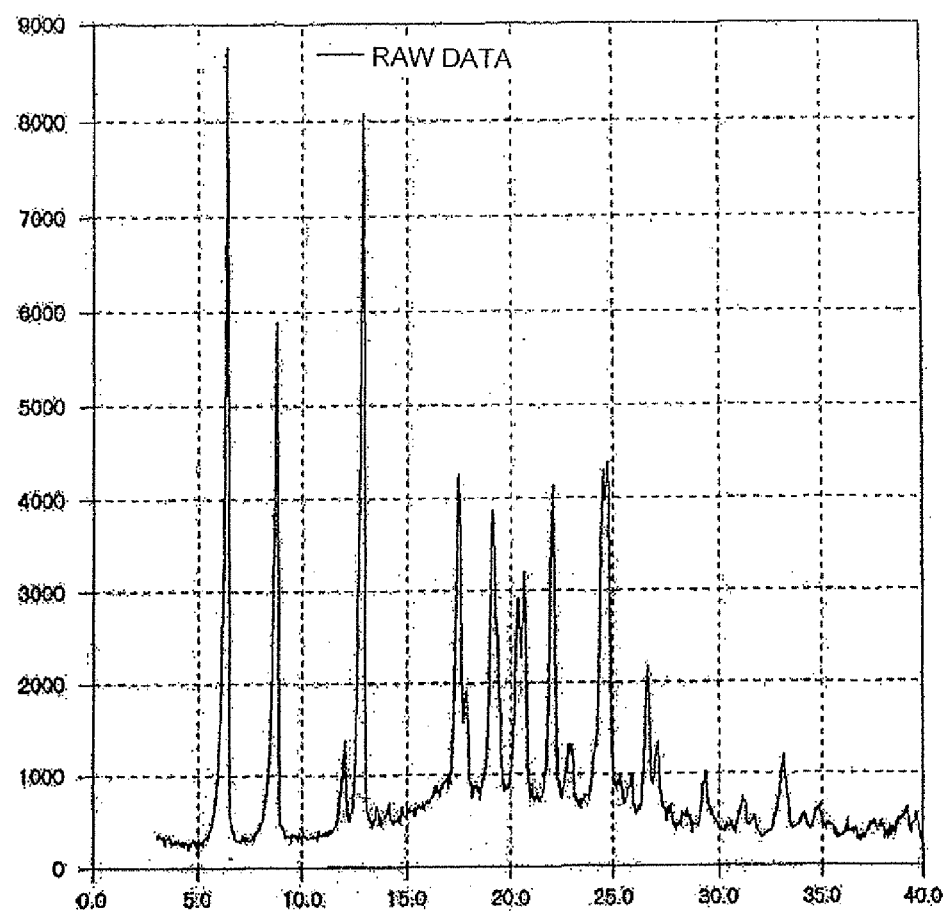
FIG. 2 is a figure showing a powder X-ray diffractogram of a B-form crystal of (3R,4S)-7-hydroxymethyl-2,2,9-trimethyl-4-(phenethylamino)-3,4-dihydro-2H-pyrano[2,3-g]quinolin-3-ol obtained according to the present invention.

Production of a B-Form Crystal of (3R,4S)-7-hydroxymethyl-2,2,9-trimethyl-4-(phenethylamino)-3,4-dihydro-2H-pyrano[2,3-g]quinolin-3-ol 62.23 g of an A-form crystal of (3R,4S)-7-hydroxymethyl-2,2,9-trimethyl-4-(phenethylamino)-3,4-dihydro-2H-pyrano[2,3-g]quinolin-3-ol was dissolved in 247.73 g of ethanol with heating the mixture to 62° C. To the resultant solution, 275.19 g of water was dropped at a temperature of 55 to 67° C. over 20 minutes, and the resultant mixture was cooled down to 5° C. over 3 hours, followed by stirring the mixture at the same temperature for 30 minutes to filter off the crystal. The crystal was dried at 50° C. under reduced pressure until the weight of the crystal was not lost on drying, and 59.22 g of a white solid was produced. The obtained crystal was subjected to DSC analysis and as the result, an endothermic peak was confirmed at 91° C. In the powder X-ray diffractogram of the crystal, characteristic peaks were observed at diffraction angles (2θ) of 6.4, 8.7, 12.8, 17.5, 19.1, 20.7, 22.0, 24.8, 26.6. The result is shown in FIG. 2. In addition, the crystal was subjected to the measurement of water content using a Karl Fischer moisture meter (volumetric analysis), and as a result, water content of 3.2% by mass was detected.

Example 3

Figure 3:
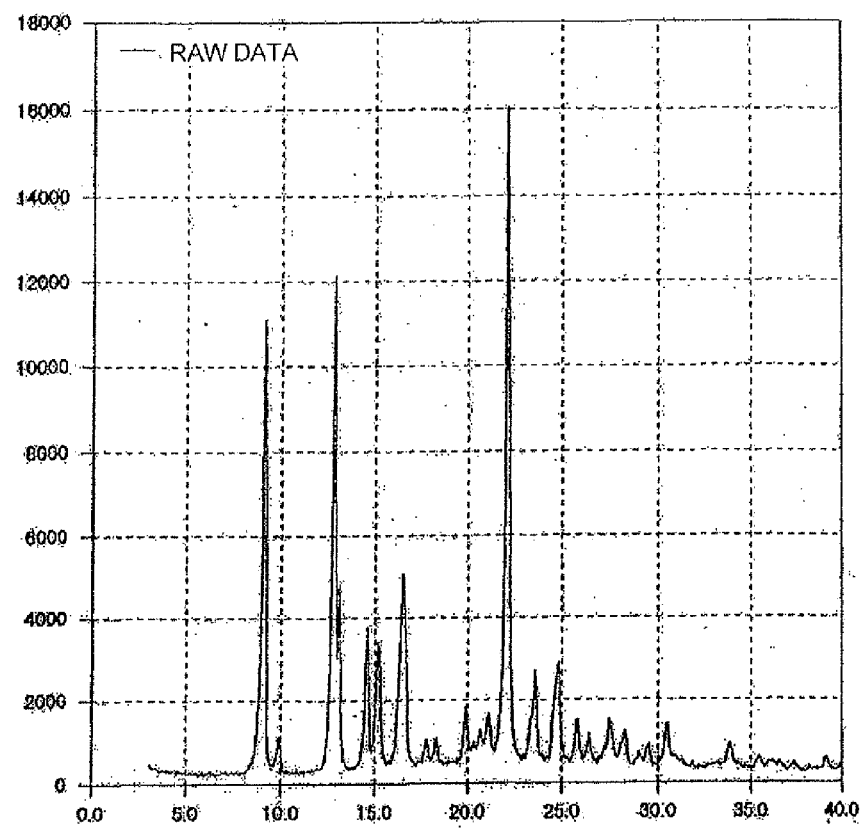
FIG. 3 is a figure showing a powder X-ray diffractogram of an E-form crystal of (3R,4S)-7-hydroxymethyl-2,2,9-trimethyl-4-(phenethylamino)-3,4-dihydro-2H-pyrano[2,3-g]quinolin-3-ol obtained according to the present invention.

Production of an E-Form Crystal of (3R,4S)-7-hydroxymethyl-2,2,9-trimethyl-4-(phenethylamino)-3,4-dihydro-2H-pyrano[2,3-g]quinolin-3-ol 14.99 g of an A-form crystal of (3R,4S)-7-hydroxymethyl-2,2,9-trimethyl-4-(phenethylamino)-3,4-dihydro-2H-pyrano[2,3-g]quinolin-3-ol was dissolved in 75 mL of ethyl acetate with heating the mixture to 63° C. Thereafter, the heating was terminated and to the resultant solution, 300 mL of n-heptane of room temperature was added all at once, followed by cooling down the resultant mixture to 26° C. The resultant mixture was stirred as it was for 1 hour to filter off the crystal. The crystal was dried at 40° C. under reduced pressure to produce 12.67 g of a yellow granular solid. The obtained crystal was subjected to DSC analysis and as the result, an endothermic peak was confirmed at 119° C. In the powder X-ray diffractogram of the crystal, characteristic peaks were observed at diffraction angles (2θ) of 9.1, 12.8, 13.1, 14.6, 15.2, 16.4, 22.1, 23.6, 24.8. The result is shown in FIG. 3.

Example 4

Figure 4:
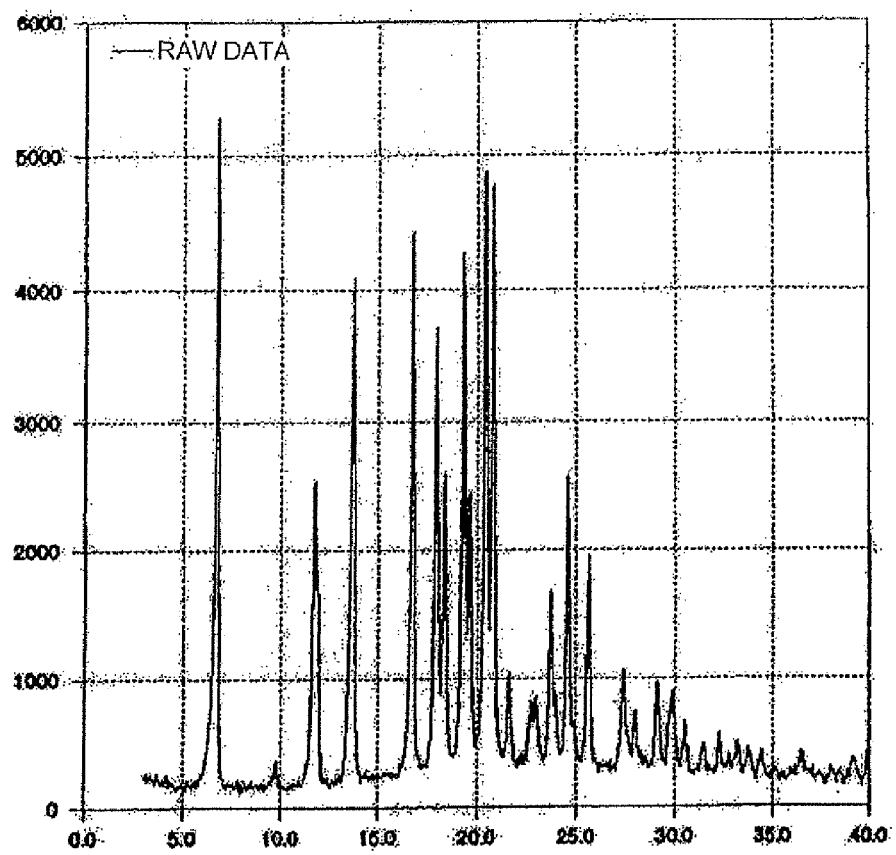
FIG. 4 is a figure showing a powder X-ray diffractogram of an F-form crystal of (3R,4S)-7-hydroxymethyl-2,2,9-trimethyl-4-(phenethylamino)-3,4-dihydro-2H-pyrano[2,3-g]quinolin-3-ol obtained according to the present invention.

Production of an F-Form Crystal of (3R,4S)-7-hydroxymethyl-2,2,9-trimethyl-4-(phenethylamino)-3,4-dihydro-2H-pyrano[2,3-g]quinolin-3-ol 10.01 g of an A-form crystal of (3R,4S)-7-hydroxymethyl-2,2,9-trimethyl-4-(phenethylamino)-3,4-dihydro-2H-pyrano[2,3-g]quinolin-3-ol was dissolved in 60.20 g of ethanol with heating the mixture to 76° C. The resultant solution was cooled down to 5° C. over 1 hour and 45 minutes, and stirred at 5° C. for 1 hour to filter off the crystal. The crystal was dried at 50° C. under reduced pressure until the weight of the crystal was not lost on drying, and 10.96 g of a white solid was produced. The obtained crystal was subjected to DSC analysis and as the result, an endothermic peak was confirmed at 99° C. In addition, in the powder X-ray diffractogram of the crystal, characteristic peaks were observed at diffraction angles (2θ) of 6.8, 11.7, 13.7, 16.8, 18.0, 19.3, 20.4, 20.8, 24.6, 25.6. The result is shown in FIG. 4.

In addition, the solution of the crystal in $CDCl_3$ with tetramethylsilane as an internal standard was measured by $^1$H-NMR. The ratio of an integration value of 2 protons of ethanol detected at δ 3.7 ppm to that of 1 proton of 4-position of Compound (1) was 2.4 to 1, so that the crystal was confirmed to be a 1.2 ethanol solvate.

Example 5

Production of a G-Form Crystal of (3R,4S)-7-hydroxymethyl-2,2,9-trimethyl-4-(phenethylamino)-3,4-dihydro-2H-pyrano[2,3-g]quinolin-3-ol 1.00 g of an A-form crystal of (3R,4S)-7-hydroxymethyl-2,2,9-trimethyl-4-(phenethylamino)-3,4-dihydro-2H-pyrano[2,3-g]quinolin-3-ol was suspended in 5 mL of 2-propanol and stirred at 21° C. for 19.7 hours. The crystal was filtered off and dried at 40° C. for 6 hours under reduced pressure until the weight of the crystal was not lost on drying, and 0.97 g of a white crystal was produced. The obtained crystal was subjected to DSC analysis and as the result, an endothermic peak was confirmed at 75.9° C.

Figure 5:
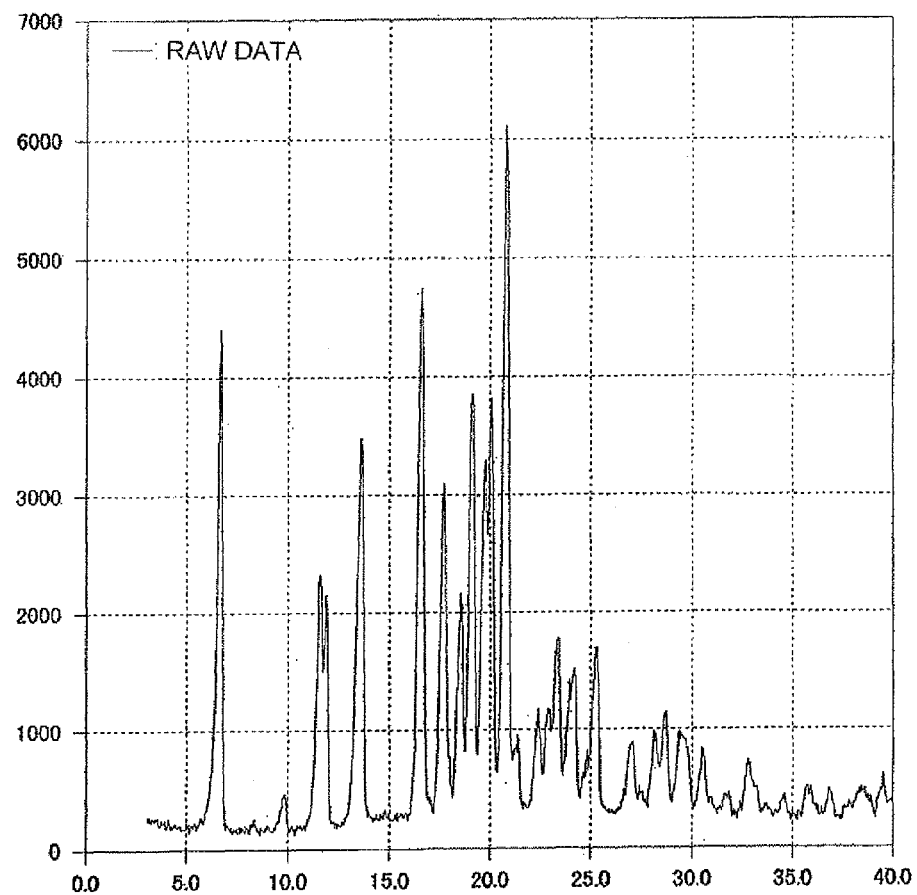
FIG. 5 is a figure showing a powder X-ray diffractogram of a G-form crystal of (3R,4S)-7-hydroxymethyl-2,2,9-trimethyl-4-(phenethylamino)-3,4-dihydro-2H-pyrano[2,3-g]quinolin-3-ol obtained according to the present invention.

In the powder X-ray diffractogram of the crystal, characteristic peaks were observed at diffraction angles (2θ) of 6.7, 11.6, 11.9, 13.6, 16.6, 17.7, 18.6, 19.1, 19.8, 20.1, 20.8. The result is shown in FIG. 5.

In addition, the solution of the crystal in $CDCl_3$ with tetramethylsilane as an internal standard was measured by $^1$H-NMR. The ratio of an integration value of 1 proton of 2-propanol detected at δ 4.0 ppm to that of 1 proton of 4-position of Compound (1) was 0.83 to 1, so that the crystal was confirmed to be a 0.83 2-propanol solvate.

Example 6

Production of an H-Form Crystal of (3R,4S)-7-hydroxymethyl-2,2,9-trimethyl-4-(phenethylamino)-3,4-dihydro-2H-pyrano[2,3-g]quinolin-3-ol 19.95 g of an A-form crystal of (3R,4S)-7-hydroxymethyl-2,2,9-trimethyl-4-(phenethylamino)-3,4-dihydro-2H-pyrano[2,3-g]quinolin-3-ol was dissolved in 140 mL of dioxane. An insoluble material was filtered off, and washed with 60 mL of dioxane. The solvent was distilled off under reduced pressure to obtain 50 g of a residual solution. The residual solution was heated to 60° C., and then 600 mL of cyclohexane was added all at once and the solution was subjected to crash cooling from 60° C. to 28° C. The solution was stirred at 25° C. to 28° C. for 5.1 hours to filter off the crystal. The crystal was dried at 50° C. for 2 hours under reduced pressure until the weight of the crystal was not lost on drying, and 21.96 g of a white crystal was produced. The obtained crystal was subjected to DSC analysis and as the result, an endothermic peak was confirmed at 80.1° C. and 86.1° C.

Figure 6:
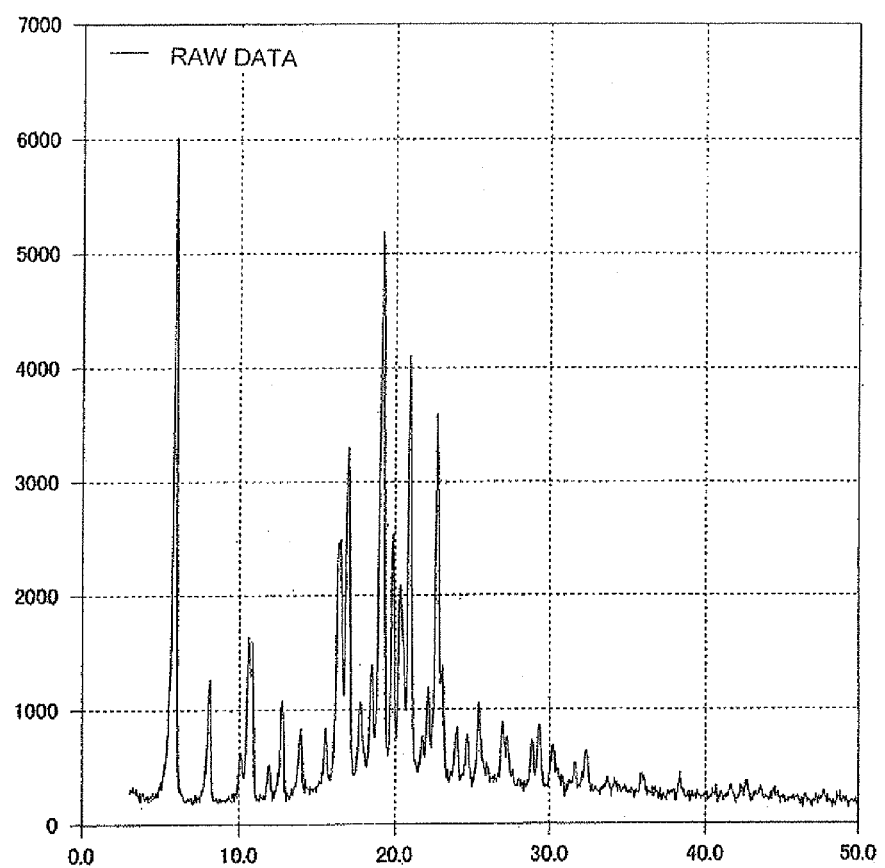
FIG. 6 is a figure showing a powder X-ray diffractogram of an H-form crystal of (3R,4S)-7-hydroxymethyl-2,2,9-trimethyl-4-(phenethylamino)-3,4-dihydro-2H-pyrano[2,3-g]quinolin-3-ol obtained according to the present invention.

In addition, in the powder X-ray diffractogram of the crystal, characteristic peaks were observed at diffraction angles (2θ) of 6.0, 16.4, 17.0, 19.2, 19.8, 20.3, 21.0, 22.8. The result is shown in FIG. 6.

In addition, the solution of the crystal in $CDCl_3$ with tetramethylsilane as an internal standard was measured by $^1$H-NMR. The ratio of an integration value of 12 protons of cyclohexane detected at δ 1.4 ppm to that of 3 protons of methyl of Compound (1) was 2.69 to 1, so that the crystal was confirmed to be a 0.67 cyclohexane solvate.

TEST EXAMPLES

Hereinafter, Test Examples using crystal forms A, B, E and F obtained by the above methods of Examples 1 to 4 are described.

Test Example 1

The thermostability, humidity stability and photostability of the A-, B- and F-form crystals of Compound (1) were examined.

The conditions for each test were as follows.
Thermostability test: 60° C., humidity was not controlled, 2 weeks, in air-tight container
Humidity stability test: 25° C., 90% RH, 2 weeks, in opened container
Photostability test: 200 W/m²·hr, 25° C., 60% RH, 57 hours, in opened container In addition, the stability of the crystals was evaluated by the degree of increase of the total amount of impurities by HPLC analysis. The result is shown in Table 1.

TABLE 1

|  | A-form crystal | B-form crystal | F-form crystal |
|---|---|---|---|
| Initial value | 0.84% | 0.55% | 0.25% |
| Thermostability | 0.83% | 1.70% | 0.37% |
| Humidity stability | 0.83% | 0.53% | 0.35% |
| Photostability | 0.85% | 0.72% | 0.74% |

In every crystal form, the increase of impurities under the conditions was 1.5% or less. It is confirmed that the A-form crystal among them is the most stable as no increase of impurities under the conditions.

Test Example 2

The A-, B- and E-form crystals of Compound (1) were subjected to an acceleration test. The conditions for the test were as follows.
Acceleration test: 40° C., 75% RH, 6 months, in an air-tight container
[Measurement Conditions]

In addition, the stability of the crystals was evaluated by the degree of increase of the total amount of impurities by HPLC analysis. The result is shown in Table 2.

TABLE 2

|  | A-form crystal | B-form crystal | E-form crystal |
|---|---|---|---|
| Initial value | 0.70% | 0.42% | 0.64% |
| Measured value after test | 0.80% | 1.15% | 0.64% |

In every crystal form, the increase of impurities under the conditions for acceleration test was 1.5% or less. A-form and E-form crystals were confirmed to be remarkably stable because no increase of impurities in them was observed.

Test Example 3

The A-, B- and E-form crystals of Compound (1) were evaluated by water adsorption analysis.

[Measurement conditions] sample amount: 0.2 g; pre-treatment: 60° C., 20 hours; temperature 25° C., Volumetric adsorption apparatus (trade name: BELSORP 18 manufactured by BEL Japan, Inc.) was used.

Figure 7:
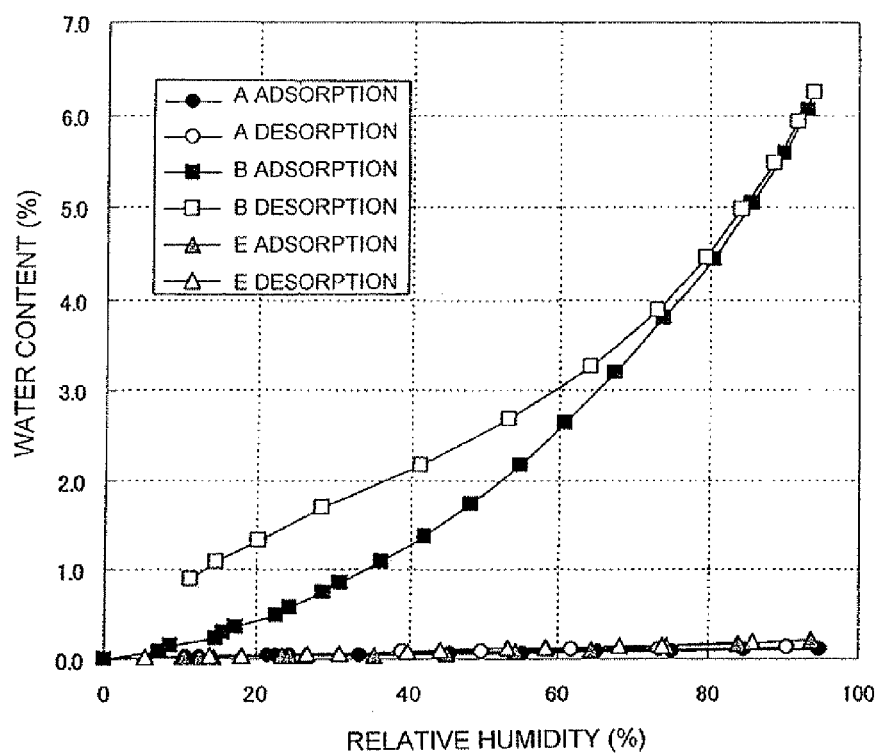
FIG. 7 is a figure showing water adsorption isotherms of A-, B- and E-form crystals of (3R,4S)-7-hydroxymethyl-2,2,9-trimethyl-4-(phenethylamino)-3,4-dihydro-2H-pyrano[2,3-g]quinolin-3-ol obtained according to the present invention.

In the B-form crystal, although the adsorption of water was observed, the adsorption was reversible. In the A-form and E-form crystals, there was observed no adsorption of water. It was observed that the adsorption of water on A-form crystal was less than that on E-form crystal. The result is shown in FIG. 7.

Test Example 4

The solubility and the specific surface area of the A-form, B-form, E-form and F-form crystals of Compound (1) were examined.
Solubility
[Measurement conditions] JP2, pH 6.8 (3.40 g of potassium dihydrogen phosphate and 3.55 g of anhydrous disodium hydrogen phosphate is dissolved in water to obtain 1 liter of solution. The 1 volume of the solution is mixed with the 1 volume of water to obtain JP2, pH 6.8.), 60 minutes
according to the Japanese Pharmacopoeia fifteenth edition, dissolution test (Protocol of the dissolution test; sample amount: 10 mg, test solution: JP2, pH 6.8, 500 mL, sampling point: 5, 15, 30, 60 min, paddle rotational speed: 100 ppm, bath temperature: 37° C.)
Specific Surface Area
[Measurement conditions] adsorption temperature: 77K, adsorption equilibrium time: 300 seconds
[Measured value unit] square meter/gram
The measurement was performed by the BET method using the nitrogen adsorption in liquid nitrogen after a pre-treatment in refluxed liquid nitrogen. The result is shown in Table 3.

TABLE 3

|  | A-form crystal | B-form crystal | E-form crystal | F-form crystal |
|---|---|---|---|---|
| Solubility | 36% | 27% | 23% | 30% |
| Specific surface area | 0.7 | 0.3 | 0.3 | — |

("—" in Table 3 means "unmeasured".)

Every crystal form was soluble in the JP2 solution. Particularly, the A-form crystal had high solubility. In addition, the A-form crystal also exhibited a high value of the specific surface area.

It is surprising that the A-form crystal has excellent stability and high solubility. In addition, it can be said that the A-form crystal possesses excellent characteristic as a drug.

Test Example 5

Figure 8:
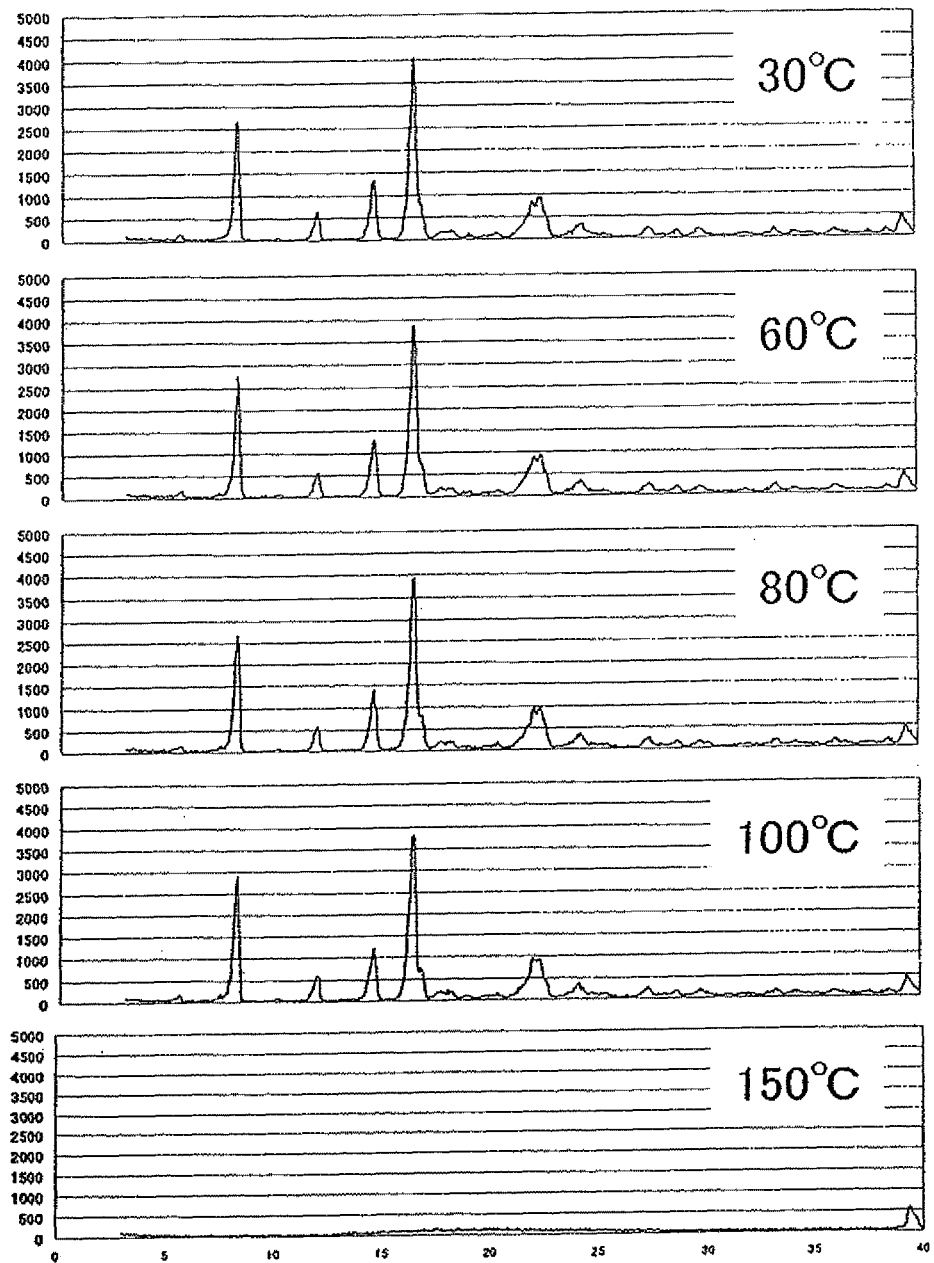
FIG. 8 is a figure showing the high-temperature X-ray diffractogram of the A-form crystal of (3R,4S)-7-hydroxymethyl-2,2,9-trimethyl-4-(phenethylamino)-3,4-dihydro-2H-pyrano[2,3-g]quinolin-3-ol obtained according to the present invention.
Figure 9:
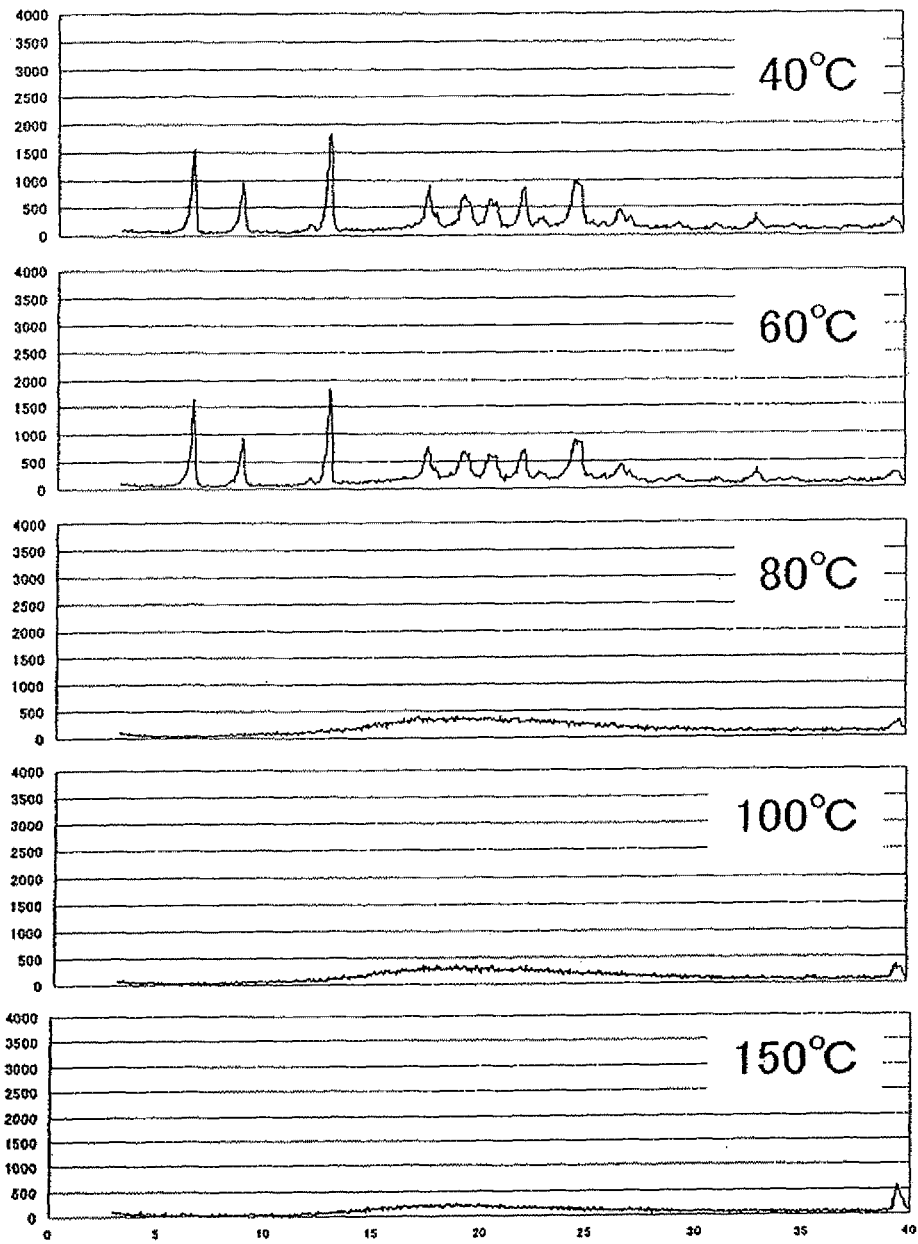
FIG. 9 is a figure showing the high-temperature X-ray diffractogram of the B-form crystal of (3R,4S)-7-hydroxymethyl-2,2,9-trimethyl-4-(phenethylamino)-3,4-dihydro-2H-pyrano[2,3-g]quinolin-3-ol obtained according to the present invention.

The A-form and B-form crystals of Compound (1) were subjected to the high-temperature XRD measurement.
As shown in FIG. 8 and FIG. 9, there was observed no change until 100° C. in the powder X-ray diffractogram of the A-form crystal and until 60° C. in the powder X-ray diffractogram of the B-form crystal. Particularly, the A-form crystal was considered to exhibit satisfactory stability as a drug.

INDUSTRIAL APPLICABILITY

According to the present invention, there can be provided a method capable of producing a chemically stable compound having the same quality and the same crystal form as those of (3R,4S)-7-hydroxymethyl-2,2,9-trimethyl-4-(phenethylamino)-3,4-dihydro-2H-pyrano[2,3-g]quinolin-3-ol useful as a drug, and novel crystal forms thereof.

The invention claimed is:
1. A crystal form of (3R,4S)-7-hydroxymethyl-2,2,9-trimethyl-4-(phenethylamino)-3,4-dihydro-2H-pyrano[2,3-g]quinolin-3-ol of Formula (1):

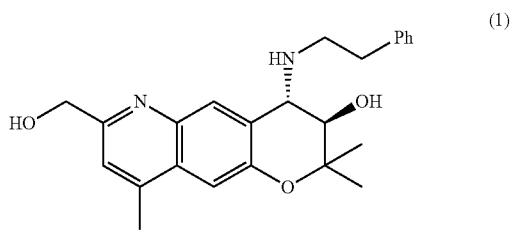 [SMILES: Cc1cc(CO)nc2cc3c(cc12)OC(C)(C)[C@H](O)[C@H]3NCCc1ccccc1]

wherein the crystal form is selected from the group consisting of:
an A-form having characteristic peaks at diffraction angles (2θ) of 5.6, 8.2, 12.0, 14.7, 16.6, 16.9, 17.9, 18.4, 22.5, 24.5, and 27.6 in a powder X-ray diffractogram of the crystal;
a B-form having characteristic peaks at diffraction angles (2θ) of 6.4, 8.7, 12.8, 17.5, 19.1, 20.7, 22.0, 24.8, and 26.6 in a powder X-ray diffractogram of the crystal;
a E-form having characteristic peaks at diffraction angles (2θ) of 9.1, 12.8, 13.1, 14.6, 15.2, 16.4, 22.1, 23.6, and 24.8 in a powder X-ray diffractogram of the crystal;
a F-form having characteristic peaks at diffraction angles (2θ) of 6.8, 11.7, 13.7, 16.8, 18.0, 19.3, 20.4, 20.8, 24.6, and 25.6 in a powder X-ray diffractogram of the crystal;
a G-form having characteristic peaks at diffraction angles (2θ) of 6.7, 11.6, 11.9, 13.6, 16.6, 17.7, 18.6, 19.1, 19.8, 20.1, and 20.8 in a powder X-ray diffractogram of the crystal; and
a H-form having characteristic peaks at diffraction angles (2θ) of 6.0, 16.4, 17.0, 19.2, 19.8, 20.3, 21.0, and 22.8 in a powder X-ray diffractogram of the crystal.
2. The crystal of claim 1, wherein the crystal is in the A-form having characteristic peaks at diffraction angles (2θ) of 5.6, 8.2, 12.0, 14.7, 16.6, 16.9, 17.9, 18.4, 22.5, 24.5, and 27.6 in a powder X-ray diffractogram of the crystal.
3. The crystal of claim 1, wherein the crystal is in the B-form having characteristic peaks at diffraction angles (2θ) of 6.4, 8.7, 12.8, 17.5, 19.1, 20.7, 22.0, 24.8, and 26.6 in a powder X-ray diffractogram of the crystal.
4. The crystal of claim 1, wherein the crystal is in the E-form having characteristic peaks at diffraction angles (2θ) of 9.1, 12.8, 13.1, 14.6, 15.2, 16.4, 22.1, 23.6, and 24.8 in a powder X-ray diffractogram of the crystal.
5. The crystal of claim 1, wherein the crystal is in the F-form having characteristic peaks at diffraction angles (2θ) of 6.8, 11.7, 13.7, 16.8, 18.0, 19.3, 20.4, 20.8, 24.6, and 25.6 in a powder X-ray diffractogram of the crystal.
6. The crystal of claim 1, wherein the crystal is in the G-form having characteristic peaks at diffraction angles (2θ) of 6.7, 11.6, 11.9, 13.6, 16.6, 17.7, 18.6, 19.1, 19.8, 20.1, and 20.8 in a powder X-ray diffractogram of the crystal.
7. The crystal of claim 1, wherein the crystal is in the H-form having characteristic peaks at diffraction angles (2θ) of 6.0, 16.4, 17.0, 19.2, 19.8, 20.3, 21.0, and 22.8 in a powder X-ray diffractogram of the crystal.

8. A production method of the crystal of claim 2, comprising crystallizing the compound of Formula (1) in an ester solvent.

9. A production method of the crystal of claim 2, comprising crystallizing the compound of Formula (1) in an aliphatic hydrocarbon solvent.

10. A production method of the crystal of claim 2, comprising crystallizing the compound of Formula (1) in a nitrile solvent.

11. A production method of the crystal of claim 2, comprising crystallizing the compound of Formula (1) in an aromatic hydrocarbon solvent.

12. A production method of the crystal of claim 2, comprising crystallizing the compound of Formula (1) in a ketone solvent.

13. A production method of the crystal of claim 3, comprising crystallizing the compound of Formula (1) from a water-containing organic solvent.

14. A production method of the crystal of claim 4, comprising:
    heating and dissolving the compound of Formula (1) in an acetate ester solvent or a ketone solvent; and
    performing one shot addition of an aliphatic hydrocarbon solvent and crash cooling.

15. A production method of the crystal of claim 5, comprising crystallizing the compound of Formula (1) from ethanol.

16. A production method of the crystal of claim 6, comprising crystallizing the compound of Formula (1) from 2-propanol.

17. A production method of the crystal of claim 7, comprising:
    heating and dissolving the compound of Formula (1) in an ether solvent; and
    performing one shot addition of cyclohexane and crash cooling.

18. A production method of the crystal of claim 2, characterized in that the compound of Formula (1) is dissolved in an ester solvent followed by adding an aliphatic hydrocarbon solvent to be crystallized.

19. A production method of the crystal of claim 18, characterized in that the compound of Formula (1) is dissolved in ethyl acetate solvent followed by adding heptane to be crystallized.

20. A production method of the crystal of claim 19, characterized by cooling down 0-5° C. after adding heptane.

21. A production method of the crystal of claim 14, wherein the acetate ester solvent or the ketone solvent is ethyl acetate and the aliphatic hydrocarbon solvent is heptane.

* * * * *